United States Patent [19]

Spratt

[11] Patent Number: 5,724,973

[45] Date of Patent: Mar. 10, 1998

[54] METHOD AND APPARATUS FOR AUTOMATED VASCULAR DIAMETER DETERMINATION

[75] Inventor: Ray Steven Spratt, San Jose, Calif.

[73] Assignee: Diasonics Ultrasound, Inc., Santa Clara, Calif.

[21] Appl. No.: 705,333

[22] Filed: Aug. 29, 1996

[51] Int. Cl.$^6$ ...................................................... A61B 8/00
[52] U.S. Cl. ...................... 128/661.03; 128/922
[58] Field of Search .................... 128/660.07, 660.01, 128/661.01, 661.1, 661.03; 382/128, 266, 270–273

[56] References Cited

U.S. PATENT DOCUMENTS

| | | | |
|---|---|---|---|
| 5,148,809 | 9/1992 | Biegeleisen-Knight et al. | 128/660.07 |
| 5,280,787 | 1/1994 | Wilson et al. | 128/661.1 |
| 5,303,706 | 4/1994 | Moshfeghi | 128/653.2 |
| 5,322,067 | 6/1994 | Prater et al. | 128/661.1 X |
| 5,495,852 | 3/1996 | Stadler et al. | 128/661.1 X |
| 5,555,886 | 9/1996 | Weng et al. | 128/661.1 |

OTHER PUBLICATIONS

Geiser, E.A. "Applications of Automatic Edge Detection And Image Enhancement Techniques to Two–Dimensional Echocardiography".

*Primary Examiner*—Francis Jaworski
*Attorney, Agent, or Firm*—Blakely, Sokoloff Taylor & Zafman

[57] ABSTRACT

A method and apparatus for automated measuring of a diameter of a first region enclosed in a second region internal to a living organism, wherein the first and second regions consist of different cellular matter. One embodiment of the invention includes generating a plurality of trial diameters, wherein each trial diameter includes an inner and outer region and has a different length. An ultrasonic measurement is taken of the inner region and the outer region for each trial diameter. The difference is determined for the ultrasonic measurements corresponding to the inner and outer regions of each trial diameter. The trial diameter which most closely corresponds to the diameter of the first region is then selected, wherein the difference of the ultrasonic measurements corresponding to the inner and outer regions is greatest for the trial diameter which most closely corresponds to the diameter of the first region.

18 Claims, 3 Drawing Sheets

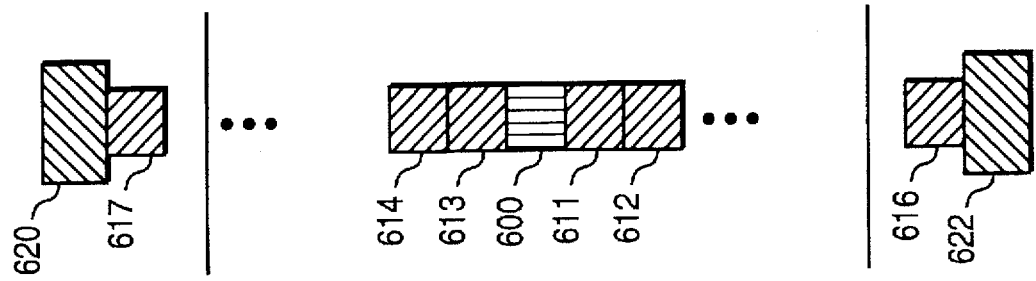
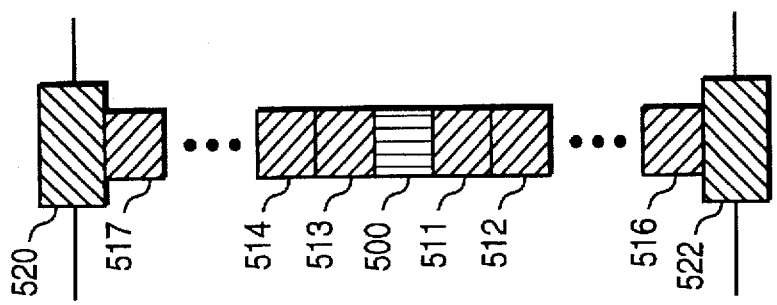
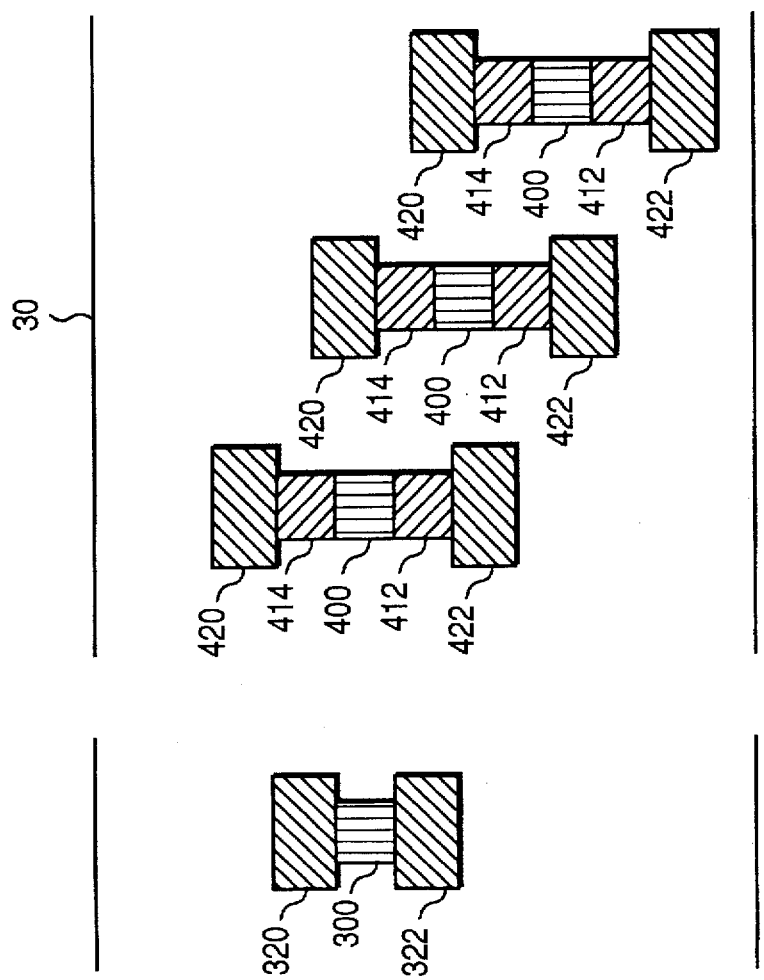

METHOD AND APPARATUS FOR AUTOMATED VASCULAR DIAMETER DETERMINATION

FIELD OF THE INVENTION

The present invention relates to ultrasonic measurement equipment, and more specifically, to a method and apparatus for automated vascular diameter determination.

BACKGROUND

Measuring the volume of blood flowing through a vessel is important in diagnosing and treating vascular disease. In order to measure the volume of blood flow, the area of a vessel is first determined. There are at least two common methods for typically determining the area of a vessel.

The first method is to scan the vessel under study in the transverse plane. This allows an area of the vessel to be estimated using either a perimeter outlining method or by fitting an ellipse to the vessel border. The second method includes scanning the vessel sagitally and measuring the diameter to obtain the area of the vessel.

These prior methods of measuring the diameter, however, are difficult to perform accurately and are time consuming. The accuracy of both methods are dependent on the skill of the operator in properly measuring the vessel to be measured, and therefore, do not generate consistent, repeatable results.

Therefore, it would be desirable to have a method and apparatus for automatically determining the vascular diameter in order to eliminate some of the dependency on the skills of an operator measuring the diameter of a vessel.

SUMMARY OF THE INVENTION

One embodiment of the present invention provides a method and apparatus for automated measuring of a vessel diameter. One embodiment of the invention includes generating a plurality of trial diameters, wherein each trial diameter includes an inner and outer region and has a different length. An ultrasonic measurement is taken of the inner region and the outer region for each trial diameter. The difference is determined for the ultrasonic measurements corresponding to the inner and outer regions of each trial diameter. The trial diameter which most closely corresponds to the vessel diameter is then selected, wherein the difference of the ultrasonic measurements corresponding to the inner and outer regions is greatest for the trial diameter which most closely corresponds to the vessel diameter.

BRIEF DESCRIPTION OF THE DRAWINGS

One embodiment of present invention is illustrated by way of example, and not by way of limitation, in the figures of the accompanying drawings and in which like reference numerals refer to similar elements and in which:

FIG. 3 is an initial trial diameter in one embodiment of the present invention.

FIG. 4 is an extended trial diameter in one embodiment of the present invention.

FIG. 5 is a trial diameter in one embodiment of the present invention wherein the trial diameter is equal to the actual diameter of the vessel.

FIG. 6 is a final condition according to one embodiment of the present invention wherein the trial diameter of the vessel is at a maximum.

DETAILED DESCRIPTION

A method and apparatus is described for automatically determining vascular diameter measurements. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

In one embodiment of the invention, the vascular diameter is determined by locating the walls of the vessel by using an ultrasonic device to measure intensity level of an "inner region" known to be within the vessel, and comparing the intensity level the inner region with an "outer region" known to be outside the edges of the inner region. The outer regions are then repeatedly extended outward until the contrast between the intensity levels of the outer and inner regions is strong enough to indicate that the outer regions are aligned with the walls of the vessel.

In one embodiment of the invention, the following equation is used in order to compare ultrasonic measurements corresponding to the inner and outer regions:

$$D = \frac{|\bar{x}_{out} - \bar{x}_{in}|}{\sqrt{\sigma_{out}^2 - \sigma_{in}^2}} \qquad \text{(Equation 1)}$$

where $\bar{x}_{out}$ represents the mean ultrasonic measurement of the outer regions, and $\bar{x}_{in}$ represents the mean ultrasonic measurement of the inner region. The standard deviations of the inner and the outer regions are represented by $\sigma_{in}^2$ and $\sigma_{out}^2$, respectively. Equation 1 gives the difference in means of the outer and inner regions normalized by the average variance of the inner and outer regions. Thus, D in Equation 1 is a statistical measure of the difference between the ultrasonic signal intensity of the outer regions and the inner region. Alternative equations that allows distinction between the highly reflective vessel walls and the less reflective blood may be used.

Figure 1:
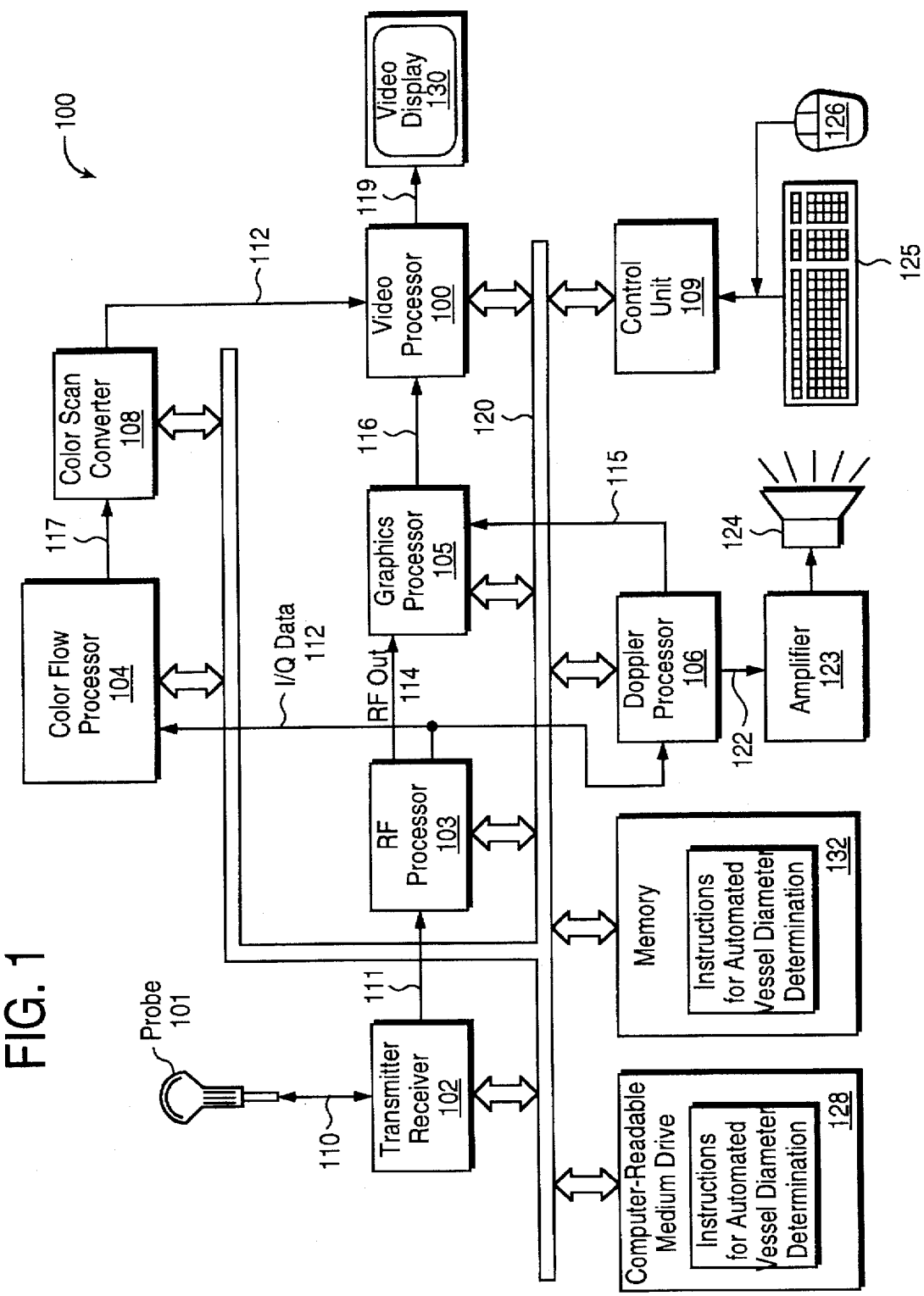
FIG. 1 is a block diagram of an ultrasonic system capable of implementing one embodiment of the present invention.

Referring to FIG. 1, an ultrasonic system capable of implementing one embodiment of the present invention is illustrated as ultrasonic system 100. Ultrasonic system 100 generally comprises a probe 101 which is coupled via line 110 to transmitter/receiver circuitry 102. Transmitter/receiver circuitry 102 is designed so that the elements of probe 101 will be fired at specified time intervals, with reflective pulses being detected using probe 101 at another given time interval. Transmitter/receiver circuitry 102 is coupled to control unit 109 via bus 120. Control unit (or host computer) 109 controls circuitry in the imaging system via bus 120. Control unit 109 is further coupled to a keyboard 125 and a mouse, trackball or other device cursor control 126 for movement and control information shown on video display 130 and for entering information and/or request to control unit 109.

Once a pulse is received by transmitter/receiver circuitry 102, such information is transmitted by line 111 to radio frequency (RF) processor 103 for further processing. The radio frequency information (in-phase (I) and quadrature (Q) signals) is further transmitted via line 114 to graphics processor 105 and to Doppler processor 106 via lines 114 and 112, respectively. Information generated by Doppler processor 106 is transmitted via line 115 to graphics processor 105. Graphics processor 105 transmits scan line information to video processor 127 via line 116 for generation of black and white ultrasound information on video display 130. Such information may be transmitted in National Television Standards Committee (NTSC) format and thus be stored on video tape for later clinical examination by attending medical personnel.

In addition to information passed to graphics processor 105 and Doppler processor 106, RF processor 103 transmits I and Q signals via line 112 to color flow processor 104. Color flow processor 104 is also controlled by control unit 109 via bus 120. Color flow processor 104 detects Doppler shift and blood flow information in living tissue, and thus transmits this information via line 117 to color scan converter 108. Color scan converter 108 interpolates point scan line information obtained from color flow processor 104, and transmits that information on line 118 to video processor 127 for representation of blood flow in the human body.

The methods of the present invention may be operative either within the graphics processor 105 or the color processor 104, processing image data.

Figure 2:
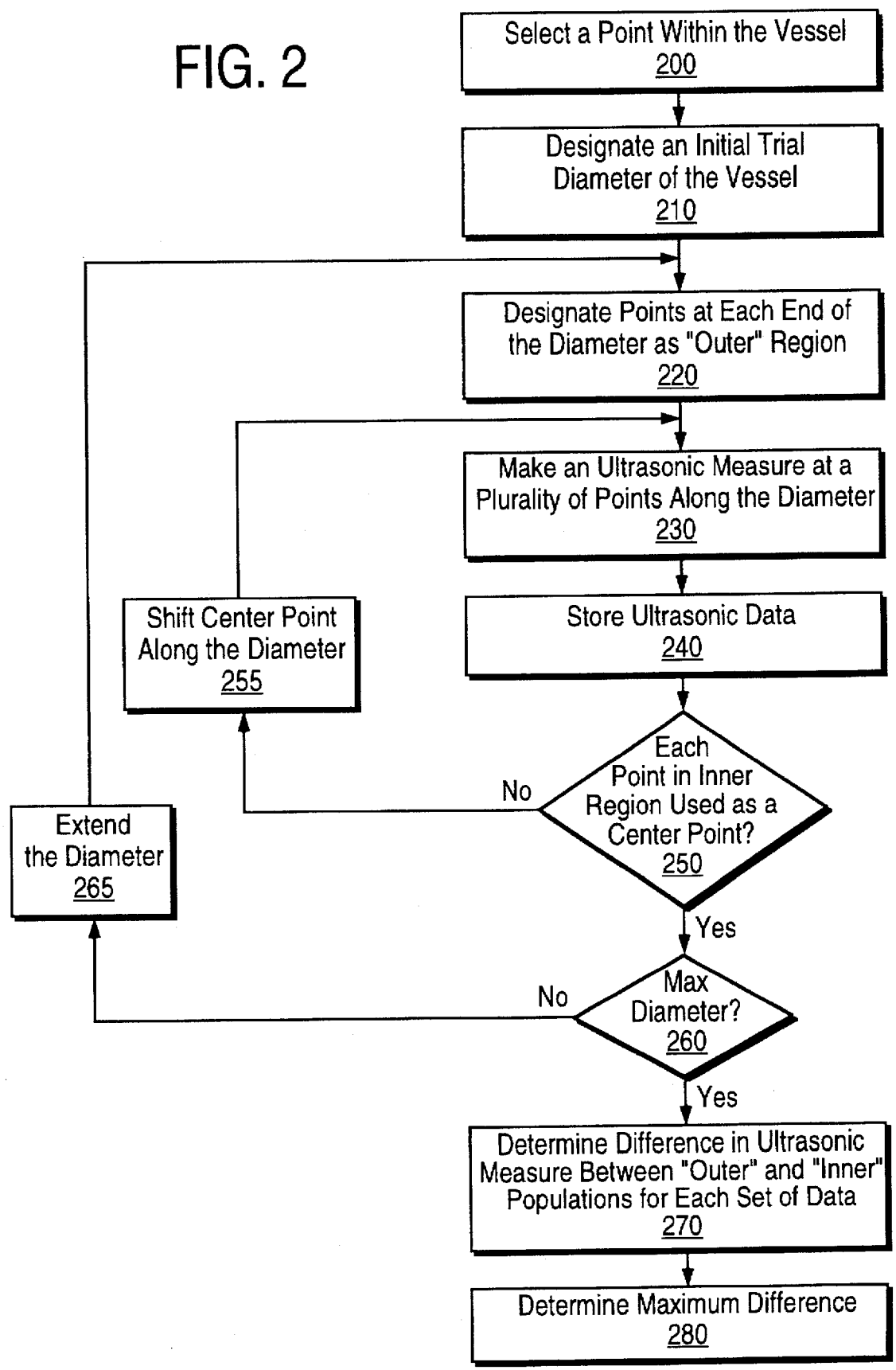
FIG. 2 is a flow diagram for one embodiment of the present invention.

FIG. 2 is a flow diagram showing the steps for determining the diameter of a vessel according to one embodiment of the present invention. In step 200, a point known to be within a vessel is selected. The selection of the point known to be within the vessel may be accomplished automatically or manually. According to one embodiment, a cursor is placed on a video display 130 of ultrasonic system 100 by an operator via an input device such as keyboard 125 or cursor control device 126. Alternatively, a point within the vessel to be measured may be selected automatically by ultrasonic system 100.

Once a point inside the vessel is selected, in step 210 an initial trial diameter is generated to determine where to measure ultrasonic intensity levels. The initial trial diameter is smaller than the actual diameter of the vessel (e.g., three to five pixels long. Moreover, the initial trial diameter typically consist of an odd number of pixels such that the diameter is symmetrical on either side of a center pixel. A units of measurement other than pixels may be used within the scope of the invention.

In step 220, a predetermined number of pixels on each end of the initial trial diameter are designated as the "outer regions." A predetermined number of pixels in the center of the initial diameter are designated as a "central point." Any remaining pixels in between the outer regions and the central point are designated as the "intermediate region." The central point along with the intermediate region comprise the "inner region."

For example, FIG. 4(a) illustrates an example of a trial diameter, however, not necessarily an initial trial diameter. In FIG. 4(a), block 400 represents the central point, blocks 420 and 422 represent the outer region, and blocks 400, 414, and 412 represent the inner region.

The initial diameter is oriented perpendicular to the flow of blood through the vessel. According to one embodiment, the direction of blood flow is obtained via Doppler signals processed by ultrasonic system 100. Alternatively, the user of ultrasonic system 100 inputs the direction of blood flow via cursor control device 126 and video display 130.

In one embodiment of the invention, the inner region of the initial trial diameter consist only of one pixel as a central point and an outer region consisting of one pixel on each opposite side of the central point. For example, FIG. 3 illustrates the initial diameter consisting of a central point 300 and outer regions 320 and 322 on opposite ends of central point 300. Central point 300 is the point known to be located within vessel 30, as designated in step 200. In alternative embodiments, however, the initial trial diameter may include an inner region of more than one pixel.

In step 230, an ultrasonic measurement is taken at each pixel along the trial diameter, including the inner and outer regions. In alternative embodiments, the ultrasonic measurements taken in step 230 may be taken at every other pixel (or what ever unit of measurement is being used). The ultrasonic measurements may be any type of ultrasonic measurement, for example, reflectivity, color, etc. In step 240, data from the ultrasonic measurements are stored in a memory device for later analysis.

In one embodiment of the invention, after an ultrasonic measurement has been taken for all the points along the trial diameter in step 230, the trial diameter is vertically shifted so that initial central point is shifted over each point of the inner region. Each time the trial diameter is shifted, step 230 is repeated to generate a new ultrasonic measurement for all the points along the shifted trial diameter, including the inner region and the outer regions. When the trial diameter is shifted the length of the trial diameter remains constant.

For example, FIG. 4(a) illustrates an unshifted trial diameter with the inner region consisting of the central point 400 and the intermediate points 410 and 412. FIG. 4(b) illustrates the trial diameter shifted downward so that the central point is located at the position of the initial lower intermediate point 412. FIG. 4(c) illustrates further illustrates the trial diameter shifted upward so that the central point 400 is located at the position of the initial upper intermediate point 414.

However, recall that in one embodiment, the inner region of the initial trial diameter only consist of a central point (as shown in FIG. 3). Therefore, in the case of this particular embodiment, the shifting of the initial trial diameter is not necessary.

In step 250, the ultrasonic system 100 determines whether the present trial diameter has been shifted so that the central point has been shifted to each point in the inner region. If the shifting of the trial diameter has not been completed for the present trial diameter, then the present trial diameter is vertically shifted in step 255 so that initial central point is shifted over each point of the inner region as described above and illustrated in FIG. 4. As stated above, each time the trial diameter is shifted, an ultrasonic measurement is generated for each point in the extended diameter.

If it is determined in step 250 that the shifting of the present trial diameter has been completed, then in step 260 the ultrasonic system 100 determines whether the present trial diameter is to be extended and have steps 220–260 repeated on the extended trial diameter. More specifically, in step 260 it is determined whether the present trial diameter has already been extended to a predetermined "maximum diameter", which is assumed to be longer than the diameter of the vessel under study.

If the present trial diameter has already been extended to the maximum diameter, the diameter of the vessel under study is determined in step 270, which is described in more detail below. If it is determined in step 260 that the present trial diameter has not been extended to the predetermined maximum diameter, then in step 265 the length of the present trial diameter is extended. The amount by which the trial diameter is extended can vary within the scope of the invention.

Steps 220–240 are then repeated as described above for the present extended diameter. More specifically, in step 230 an ultrasonic measurement is generated for each point of the present extended trial diameter. In steps 250–255, the extended trial diameter is then vertically shifted so that each point in the inner region is placed at the initial location of the central point. As stated above, each time the extended trial diameter is shifted, an ultrasonic measurement is generated for each point in the extended trial diameter.

At some point during the cycles of extending the trial diameter, the outer regions of the trial diameter become aligned with the walls of the vessels under study. For example, FIG. 5 illustrates a trial diameter wherein the outer regions 520 and 522 are aligned with the walls of a vessel.

When the outer regions 520 and 522 are aligned with the walls of the vessel being measured, Equation 1 gives the greatest value of D because $\bar{x}_{out}$ is at or near its peak value, while $\bar{x}_{in}$, $\sigma_{out}^2$ and $\sigma_{in}^2$ are less than peak values. Therefore, Equation 1 gives the largest result when outer regions 520 and 522 are aligned with the vessel walls.

Eventually the trial diameter is extended to the predetermined maximum diameter, wherein the outer regions of the present trial diameter extend beyond the walls of the vessel, as illustrated in FIG. 6.

The set of data collected for the trial diameters that extend beyond the walls of the vessel generate a result in Equation 1 that is less than the result generated in Equation 1 when the trial diameter is equivalent to the actual diameter of the vessel because the highly reflective walls of the vessel are included in $\bar{x}_{in}$ rather than in $\bar{x}_{out}$. In an alternative embodiment, the trial diameter may be increased until the results obtained from Equation 1 and the statistical measurements gathered decreases below some predetermined portion of a peak value.

Once it is determined in step 260 that the trial diameter extends beyond the vessel walls (i.e., have reached the predetermined maximum diameter), in step 270 the ultrasonic measurements taken in steps 200–260 are analyzed. More specifically, each set of data stored at each iteration of step 240 is analyzed to determine the difference in ultrasonic measurements between the outer regions and the inner region by using Equation 1 as set forth and described above.

Once D of Equation 1 is determined for each set of data, in step 280 the maximum value of D for all trial diameters is determined. The set of data corresponding to the maximum value of D corresponds to the diameter of the vessel being measured.

Some of the steps shown in FIG. 2 may be rearranged without deviating from the spirit and scope of the present invention. For example, the step of determining the difference in ultrasonic measurements between the inner and outer regions (step 270) may be performed prior to the step of storing data (step 240) such that the data that is stored is the normalized difference in means (D), rather than the raw data from the ultrasonic measurements.

In alternative embodiments, the present invention can be implemented to determine the diameter of other bodily cellular matters in addition to vessels. That is, for example, the present invention can be implemented to determine the diameter of a first region enclosed in a second region of a living organism, wherein the first and second regions consist of different cellular matter and have different echoginicity.

The present invention can also be implemented as a computer program product that could be stored on a storage medium having stored thereon instructions which can be used to program a computer to determine the diameter of a vessel according to the present invention. For example, the present invention can be stored in a memory device, as shown in the memory device coupled to the computer system 100. In addition, the storage medium could include other computer-readable mediums including, but is not limited to, floppy disks, optical disks, CD-ROMs, and magneto-optical disks, ROMs, RAMs, EPROMs, EEPROMs, magnet or optical cards, or any type of media suitable for storing electronic instructions. The instructions stored on such a computer-readable medium could be accessed via a computer-readable medium drive, such as the computer-readable medium drive 132 shown coupled to the computer system 100.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for determining a diameter of a first region enclosed in a second region internal to a living organism, wherein the first and second regions consist of different cellular matter, said method comprising the steps of:
   a) generating a plurality of trial diameters, each trial diameter within said plurality of trial diameters having an inner and outer region, and each trial diameter within said plurality of trial diameters having a different length;
   b) generating an ultrasonic measurement of the inner region and the outer region for each trial diameter within said plurality of trial diameters;
   c) determining a difference of the ultrasonic measurements corresponding to the inner and outer regions of each trial diameter of the plurality of diameters; and
   d) selecting a trial diameter from the plurality of diameters that approximately corresponds to the diameter of the first region, wherein a difference of the ultrasonic measurements for the inner and outer regions is greatest for the trial diameter approximately corresponding to the diameter of the first region, relative to other trial diameters of said plurality of trial diameters.

2. The method of claim 1, wherein the first region consist of a vessel.

3. The method of claim 1, further includes the steps of:
   e) generating a first trial diameter;
   f) generating a separate trial diameter, said separate trial diameter having a center point and a length longer than a previously generated trial diameter;
   g) vertically shifting said separate trial diameter to a new vertical position, wherein at each new vertical position the center point is placed over a different point within an inner region of the separate trial diameter; and
   h) generating an ultrasonic measurement for the inner region and the outer region of the separate trial diameter for each vertical position of the separate trial diameter.

4. The method of claim 3 wherein the steps of the generating a separate trial diameter, vertically shifting the separate trial diameter, and generating an ultrasonic measurement of the inner and outer regions of the separate trial diameter are repeated until a length of a separate trial diameter is equal to a predetermined maximum length.

5. The method of claim 3 wherein the steps of the generating a separate trial diameter, vertically shifting the separate trial diameter, and generating an ultrasonic measurement of the inner and outer regions of the separate trial diameter are repeated until a difference between of an inner and outer region of a trial diameter falls below a predetermined portion of a peak difference.

6. The method of claim 3, wherein the step of determining a difference of the ultrasonic measurements corresponding to the inner and outer regions of each trial diameter of the plurality of diameters includes using an equation consisting of $$D = \frac{|\bar{x}_{out} - \bar{x}_{in}|}{\sqrt{\sigma_{out}^2 - \sigma_{in}^2}}$$

wherein $\bar{x}_{out}$ represents a mean ultrasonic measurement of outer regions, $\bar{x}_{in}$ represents a mean ultrasonic measurement of inner regions, and $\sigma_{in}^2$ and $\sigma_{out}^2$, respectively represent a standard deviations of the inner and the outer regions, and D represents a statistical measurement of the difference between the ultrasonic measurements of the outer regions and the inner region.

7. A computer-readable medium having stored thereon a plurality of sequences of instructions, the plurality of sequences of instructions including a first sequence of instruction for determining a diameter of a first region enclosed in a second region internal to a living organism, wherein the first and second regions consist of different cellular matter, the first sequence of instructions when executed by a processor, cause said processor to perform the steps of:
 a) generating a plurality of trial diameters, each trial diameter within said plurality of trial diameters having an inner and outer region, and each trial diameter within said plurality of trial diameters having a different length;
 b) generating an ultrasonic measurement of the inner region and the outer region for each trial diameter within said plurality of trial diameters;
 c) determining a difference of the ultrasonic measurements corresponding to the inner and outer regions of each trial diameter of the plurality of diameters; and
 d) selecting a trial diameter from the plurality of diameters that approximately corresponds to the diameter of the first region, wherein a difference of the ultrasonic measurements for the inner and outer regions is greatest for the trial diameter approximately corresponding to the diameter of the first region, relative to other trial diameters of said plurality of trial diameters.

8. The computer-readable medium of claim 7, wherein the first region consist of a vessel.

9. The computer-readable medium of claim 8, wherein the first sequence of instructions further includes instructions which when executed cause the processor to perform the steps of:
 e) generating a first trial diameter;
 f) generating a separate trial diameter, said separate trial diameter having a center point and a length longer than a previously generated trial diameter;
 g) vertically shifting said separate trial diameter to a new vertical position, wherein at each new vertical position the center point is placed over a different point within an inner region of the separate trial diameter; and
 h) generating an ultrasonic measurement for the inner region and the outer region of the separate trial diameter for each vertical position of the separate trial diameter.

10. The computer-readable medium of claim 9, wherein the steps of the generating a separate trial diameter, vertically shifting the separate trial diameter, and generating an ultrasonic measurement of the inner and outer regions of the separate trial diameter are repeated until a length of a separate trial diameter is equal to a predetermined maximum length.

11. The computer-readable medium of claim 9, wherein the steps of the generating a separate trial diameter, vertically shifting the separate trial diameter, and generating an ultrasonic measurement of the inner and outer regions of the separate trial diameter are repeated until a difference between of an inner and outer region of a trial diameter falls below a predetermined portion of a peak difference.

12. The computer-readable medium of claim 9, wherein the step of determining the difference of the ultrasonic measurements corresponding to the inner and outer regions of each trial diameter of the plurality of diameters includes using an equation consisting of $$D = \frac{|\bar{x}_{out} - \bar{x}_{in}|}{\sqrt{\sigma_{out}^2 - \sigma_{in}^2}}$$

wherein $\bar{x}_{out}$ represents a mean ultrasonic measurement of outer regions, $\bar{x}_{in}$ represents a mean ultrasonic measurement of inner regions, and $\sigma_{in}^2$ and $\sigma_{out}^2$, respectively represent a standard deviations of the inner and the outer regions, and D represents a statistical measurement of the difference between the ultrasonic measurements of the outer regions and the inner region.

13. A computer system configured to determine a diameter of a first region enclosed in a second region internal to a living organism, wherein the first and second regions consist of different cellular matter, the computer system comprising:
 a first device configured to generate a plurality of trial diameters, each trial diameter within said plurality of trial diameters having an inner and outer region, and each trial diameter within said plurality of trial diameters having a different length;
 a second device configured to generate an ultrasonic measurement of the inner region and the outer region for each trial diameter within said plurality of trial diameters;
 a third device configured to determine a difference of the ultrasonic measurements corresponding to the inner and outer regions of each trial diameter of the plurality of diameters; and
 a fourth device configured to select a trial diameter from the plurality of diameters that approximately corresponds to the diameter of the first region, wherein a difference of the ultrasonic measurements for the inner and outer regions is greatest for the trial diameter approximately corresponding to the diameter of the first region, relative to other trial diameters of said plurality of trial diameters.

14. The computer system of claim 13, wherein the first region consist of a vessel.

15. The computer system of claim 13, wherein
 said first device is further configured to generate a first trial diameter, and generate a separate trial diameter, said separate trial diameter having a center point and a length longer than a previously generated trial diameter;
 said first device is further configured to vertically shifting said separate trial diameter to a new vertical position, wherein at each new vertical position the center point is placed over a different point within an inner region of the separate trial diameter; and said second device is further configured to generate an ultrasonic measurement for the inner region and the outer region of the separate trial diameter for each vertical position of the separate trial diameter.

16. The computer system of claim 15, wherein the first and second devices are configured to repeat generating a separate trial diameter, vertically shifting the separate trial diameter, and generating an ultrasonic measurement of the inner and outer regions of the separate trial diameter for each vertical position of the separate trial diameter, until a length of a separate trial diameter is equal to a predetermined maximum length.

17. The computer system of claim 15, wherein the first and second devices are configured to repeat generating a separate trial diameter, vertically shifting the separate trial diameter, and generating an ultrasonic measurement of the inner and outer regions of the separate trial diameter for each vertical position of the separate trial diameter, until a difference between of an inner and outer region of a trial diameter falls below a predetermined portion of a peak difference.

18. The computer system of claim 15, wherein said third device is further configured to determine the difference of the ultrasonic measurements corresponding to the inner and outer regions of each trial diameter of the plurality of diameters using an equation consisting of $$D = \frac{|\bar{x}_{out} - \bar{x}_{in}|}{\sqrt{\sigma_{out}^2 - \sigma_{in}^2}}$$

wherein $\bar{x}_{out}$ represents a mean ultrasonic measurement of outer regions, $\bar{x}_{in}$ represents a mean ultrasonic measurement of inner regions, and $\sigma_{in}^2$ and $\sigma_{out}^2$, respectively represent a standard deviations of the inner and the outer regions, and D represents a statistical measurement of the difference between the ultrasonic measurements of the outer regions and the inner region.

* * * * *